Figure 2:
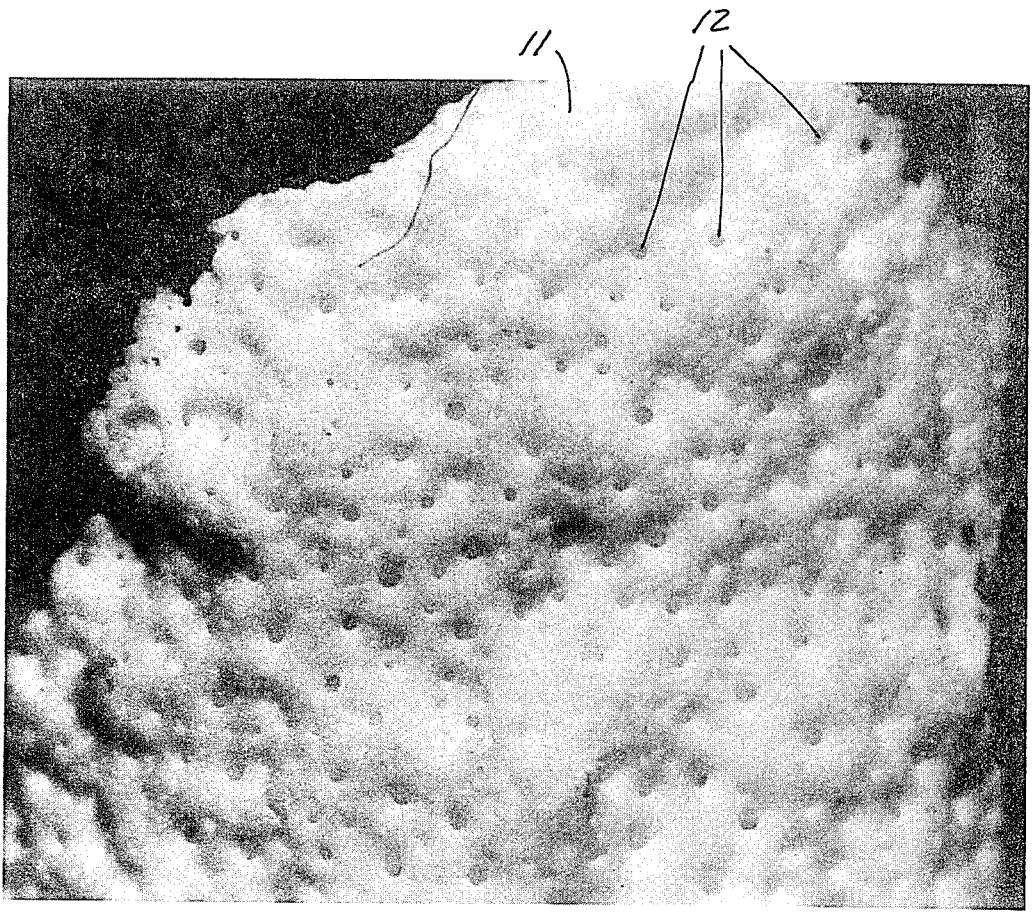

United States Patent [19]
Bryan et al.

[11] 4,073,999
[45] Feb. 14, 1978

[54] POROUS CERAMIC OR METALLIC COATINGS AND ARTICLES

[75] Inventors: Thomas Toplica Bryan, Mahtomedi Village; Arthur William Pluim, Jr., Stillwater, both of Minn.

[73] Assignee: Minnesota Mining and Manufacturing Company, St. Paul, Minn.

[21] Appl. No.: 576,110

[22] Filed: May 9, 1975

[51] Int. Cl.² .......................... A61F 1/00; B01J 21/00
[52] U.S. Cl. .................................... 428/311; 428/312; 428/332; 427/226; 427/376 A; 427/376 B; 427/376 G; 128/92 C; 3/1; 428/546; 428/548; 252/461; 252/463
[58] Field of Search ............... 427/383, 287, 226, 196, 427/191, 180, 2, 376 AB, 376 G; 29/182, 182.5; 75/200, 201; 128/92 C, 214 R; 3/1; 428/311, 312, 332; 252/461, 463

[56] References Cited
U.S. PATENT DOCUMENTS

| 3,443,261 | 5/1969 | Battista et al. .............................. 3/1 |
| 3,605,123 | 9/1971 | Hahn ..................................... 128/92 C |
| 3,662,405 | 5/1972 | Bortz et al. .................................... 3/1 |
| 3,714,071 | 1/1973 | Michalke ............................. 252/448 |
| 3,855,638 | 12/1974 | Pilliar ................................ 128/92 C |

Primary Examiner—Ralph S. Kendall
Attorney, Agent, or Firm—Cruzan Alexander; Donald M. Sell; Gary L. Griswold

[57] ABSTRACT

A method for preparing porous ceramic or metallic coatings on substrates and preparing perforated articles which are ceramic or metallic; the method involving utilization of a composition comprising ceramic powder or metallic powder, binder, and solvent whereby at least a portion of the solvent is rapidly volatilized to obtain the porosity in the ceramic or metallic material. The coated substrates and perforated articles are useful for example, as prosthetic devices, catalyst supports, and bone supplementation material.

20 Claims, 5 Drawing Figures

FIG. 1
FIG. 1A
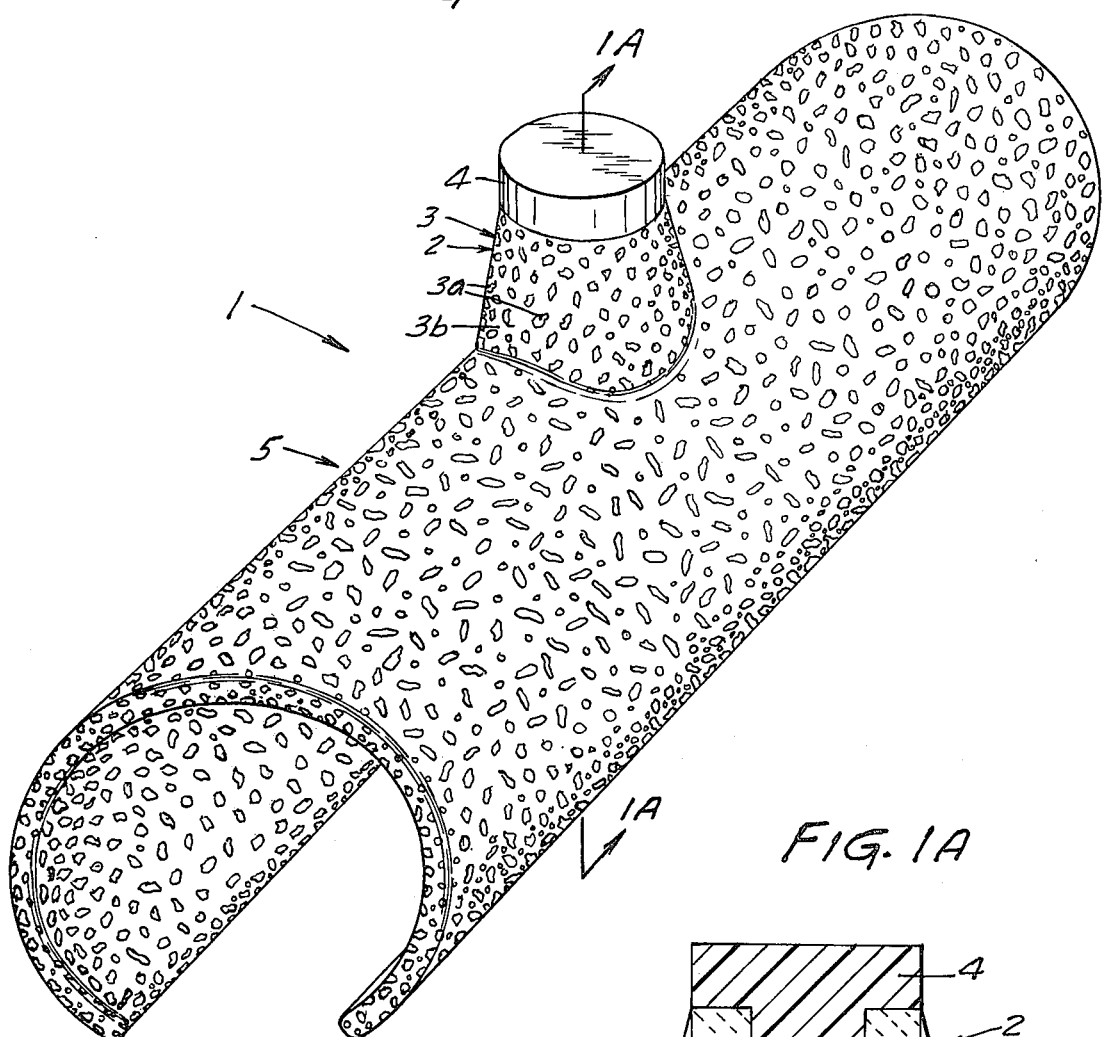
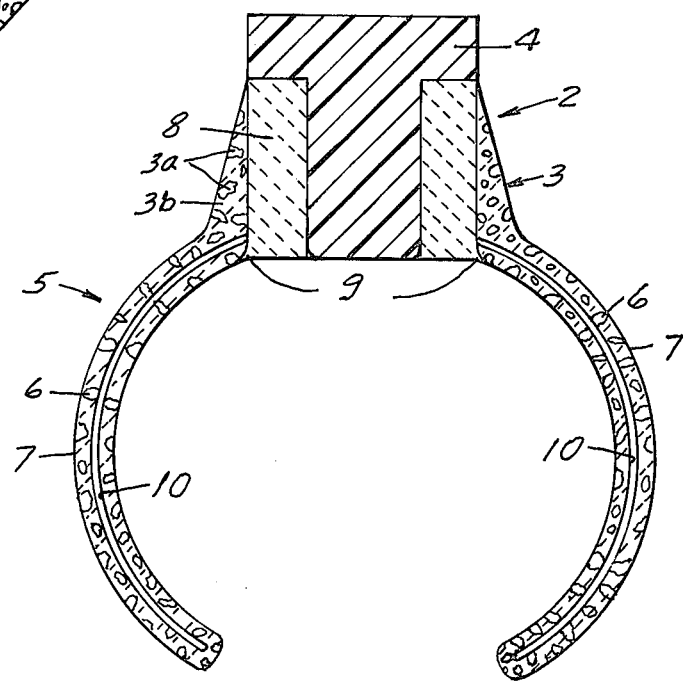

POROUS CERAMIC OR METALLIC COATINGS AND ARTICLES

This invention relates to a method for preparing porous metallic and ceramic articles and/or coated substrates. Particularly, this invention relates to prosthetic devices having a porous ceramic or metallic coating on a substrate and to perforated ceramic or metallic articles useful in or as prosthetic devices.

The use of porous ceramics in prosthetic devices is well known. In U.S. Pat. No. 3,314,420, ceramic devices comprising a porous ceramic structure are prepared by placing calcium carbonate in the ceramic. At high temperatures, i.e., on firing, the calcium carbonate decomposes into calcium oxide and carbon dioxide. The evolution of carbon dioxide causes porosity in the structure. These porous structures can be filled with plastic resin such as epoxy. The surface porosity of the articles is reinstated by leaching a portion of the uncured resin through the use of solvents. After leaching, the remainder of the resin is cured.

Another reference to preparing ceramic prosthetic devices wherein porosity is included for tissue growth and is obtained by including in the ceramic material calcium carbonate which, on firing, causes pore formation because of the evolution of carbon dioxide is "Potential of Ceramic Materials as Permanently Implantable Skeletal Prostheses" *J. Biomed. Mater. Res.* Vol. 4, pp. 433–456 (1970). Producing porosity by means of calcium carbonate, i.e., carbon dioxide, generally results in a ceramic material wherein the surface and edges of the pores are of a jagged configuration. Sharp, jagged surfaces in a prosthetic device can cause the bone to be resorbed because the body attempts to relieve high stress concentrations at the jagged surface by destruction of the bone by the body.

Porous ceramic articles have also been prepared by mixing aluminum oxide powder, water, polyvinyl alcohol and hydrogen peroxide. The mixture was placed in frames and heated until it would support itself. Then the frames were removed. Porosity was obtained by the evolution of oxygen upon the decomposition of the hydrogen peroxide. When the structures were almost dry, they were sintered. ("Compression Strength of Porous Sintered Alumina and Zirconia", *Journal of the American Ceramic Society*, Vol. 36, No. 2, February, 1953, p. 65–68).

Preparation of porous ceramics by first producing a pyrolyzable porous form which is later filled with alumina slurry is also know. (German Offenlegungsschrift No. 2,242,907).

Ceramics have been applied to substrates in a number of ways including flame spraying, sintering and die pressing and/or compaction. In flame spraying a ceramic coated structure is formed by projecting a stream of highspeed ceramic particles in a plastic state against a solid substrate. When the particles strike the cold substrate, they tend to become flat and almost instantaneously cooled so that they adhere to the substrate. Thus, the ceramic coating is built up in a layered fashion on a substrate. If small particles are used, substantial porosity is difficult to obtain. With larger particles, porosity is obtained but adhesion is not good.

In the sintering process a slurry of ceramic powder, water wetting agent, carbon particles or some other material which is capable of being destroyed by heat is placed on a substrate. The coated substrate is heated to high temperatures to burn out the pyrolyzable material, e.g., carbon particles. A porous coating is obtained by the destruction of the pyrolyzable material. However, such coatings generally have the afore-mentioned sharp edges and tend to be weak in bonding strength between the substrate and the coating.

A third method uses a ceramic powder containing a pyrolyzable material pressed onto a substrate. The coated substrate is fired at high temperatures to remove the pyrolyzable material. This method is expensive and can involve an extensive amount of machining to expose the porosity in the ceramic.

A method was sought whereby a porous coating of ceramic or metallic materials with pores having smooth edges and surfaces could be securely attached to a substrate for use in, for example, prosthetic devices, and a method was sought to prepare porous, strong ceramic or metallic articles which contained pores with smooth edges and surfaces.

A method for preparing coated substrates has been found which results in coatings with the aforementioned properties, It comprises:

(A) contacting a substrate selected from the class consisting of a ceramic substrate and metallic substrate with a composition to provide a coating of said composition on at least a portion of said substrate, said composition comprising:
  (1) 25 to 80 percent by weight of a material selected from the class consisting of ceramic powder and powdered metal wherein the number average of the longest dimension of the particles of the material is from about 0.1 to about 300 microns;
  (2) 2.0 to 12 percent by weight of a binder capable of adhering said material particles; and
  (3) 18 to 73 percent by weight solvent, at least a portion of said solvent being capable of being rapidly volatilized under the conditions of step (B);

(B) rapidly volatilizing at least a portion of said solvent of said composition on said substrate and (C) sintering said coated substrate to form a coated substrate with a porous coating.

The method for preparing a perforated article comprises:

(A) preparing a composition comprising:
  (1) 25 to 80 percent by weight of a material selected from the class consisting of ceramic powder and powdered metal wherein the number average of the longest dimension of the particles of said material is from about 0.1 to about 300 microns;
  (2) 2 to 12 percent by weight of a binder capable of adhering said material particles; and
  (3) 18 to 73 percent by weight solvent, at least a portion of said solvent being capable of being rapidly volatilized under the conditions of step (B);

(B) rapidly volatilizing at least a portion of said solvent of said composition to form a porous unfired article; and (C) sintering said article.

The first method above is particularly applicable to preparing prosthetic devices.

Before discussing the various steps of the method of the present invention, the composition which is applied to the substrate and which is utilized in preparing the perforated articles will be detailed. The composition comprises 25 to 80 percent, preferably 45 to 65 percent by weight ceramic powder or powdered metal having the number average of the longest dimension of the particles in the powder from about 0.1 to about 300 microns. When perforated articles are being prepared, the composition can contain less powder and be less viscous.

The preferred powder is ceramic powder. Ceramic powder as used herein means those materials known to the art which are available in powder form and are used to prepare solid ceramic materials. A number of ceramic powders are useful in the present invention. Exemplary useful ceramic powders include those powders of titanates, electrical porcelain, zirconates, cordierites, steatites, ferrites, spodumene, aluminum oxide, aluminum phosphate and calcium phosphates. The preferred ceramic powder is aluminum oxide which is of a grade that is 96 percent by weight pure aluminum oxide, i.e., $Al_2O_3$.

Examples of powdered metals which are useful in the present invention are powdered stainless steel, titanium, platinum, gold and alloys of these metals. The preferred powdered metal is stainless steel. The metal and ceramic of course, must be nontoxic if they are to be used in the human body and if used, as for instance, as catalyst support must be unreactive to material being reacted by the use of the catalyst which the perforated article is supporting.

The particle size of the particles in the powder as noted can vary from 0.1 to about 300 microns, but is preferably less than 30 microns, and is the number average of the longest dimension of the particles of the powder. The particles are not normally spherical. Because the strength of adhesion of the coating increases with decreasing particle size, when a coated substrate is being prepared, it is preferable to have the particle size small. However, porosity tends to decrease with decreasing particle size. Therefore, a compromise must be made between adhesion and porosity by proper choice of the particle size of the powder.

The composition contains a binder which is capable of adhering the ceramic or metallic powder particles during and after the volatilization step. The binder can be a portion of the ceramic or metallic powder which, during the volatilization step, becomes adherent to the remainder of the powder particles, e.g., aluminum phosphate. It can also be inorganic type binders such as sodium silicate which will bind the powder particles. Some of each of these types of binders are not pyrolyzable during the sintering step but may only change form during sintering and remain soluble in the human body. Therefore, their use in prosthetic devices is not preferred.

With prosthetic devices it is preferred to use a polymeric binder which is pyrolyzable during the sintering step of the process so that it is removed from the coated substrate or perforated article. The polymeric binder serves to bind the particles of the article together and in the case of a coated substrate to the substrate prior to sintering. Exemplary polymeric binders include acrylic latexes, styrene/butadiene copolymer latex, polyethylene glycol, polycarbodiimide and polyvinylpyrrolidone. The preferred binders are the acrylic latexes and styrene/butadiene latexes.

The binder normally comprises 2 to 12 percent, preferably 4 to 8 percent by weight of the composition. Sufficient binder must be available to bind the particles together during the period prior to sintering of the coated substrate or perforated article. The use of an excessive amount of binder may result in greater disruption in the coating or perforated article, and the pores produced therein may have edges and surfaces which are more jagged.

Some of the binders are added to the composition as a latex or solution. However, the percentage of binder referred to herein is the dry binder exclusive of solvent or dispersing medium. The solvent or dispersing medium which is introduced as part of the latex or solution is included in the solvent portion of the composition.

The final critical portion of the composition is the solvent. It is normally 18 to 73 percent and preferably, 35 to 55 percent by weight of the composition when coated substrates are prepared. Perforated articles can use more solvent in their preparation. Therefore, preferably 40 to 60 percent by weight solvent is used in the composition when they are being prepared. Since the solvent or a portion thereof is the means by which the porosity is obtained in the coating on the substrate or the perfroation or perforations are obtained in the perforated article, it is critical that a portion of the solvent be rapidly volatilizable under the conditions of step (B), the volatilization step, of the process. Step (B) generally involves placing the coated substrate or composition in an environment where the temperature is from about 80° to 180° C. and the pressure is atmospheric. Thus, some of the solvent generally must be rapidly volatilizable at from 80° to 180° C. and at atmospheric pressure.

A mixture of high-boiling and low-boiling solvent is preferred. The higher boiling solvents while decreasing pore size and coating thickness tend to produce coatings having a smoother and more uniform appearance. The low boiling solvents boil rapidly which is necessary in order for pore formation to occur. Exemplary useful solvents include water, propylene glycol, acetone, isopropyl alcohol, and dimethyl formamide. Generally the solvent includes water. When a latex or solvent solution is used as a binder the water or solvent from the latex or solvent solution is considered to be part of the solvent and the percentage amount given herein includes it. A preferred solvent system is one which includes 15 to 25 percent by weight water, 30 to 40 percent by weight propylene glycol, and a complemental amount of acetone.

Other ingredients can be included in the composition but are not required. One preferred additive is a salt of a long chain fatty acid having from 16 to 22 carbon atoms. It is normally present at from 1 to 4 percent by weight of the composition, if included in the composition. Exemplary salts include magnesium stearate, calcium stearate, aluminum stearate, magnesium behanate, calcium behanate and aluminum behanate. Inclusion of the salt tends to allow for more rapid removal of the solvent from the composition. Thus, pore formation occurs more readily without disruption of the coating. Other ingredients can be included in the composition which do not decrease the adhesion characteristics of the coating or the pore-forming ability of the composition.

With respect to the method, the first step in producing a coated substrate involves contacting a ceramic substrate or a metallic substrate with the composition which has been detailed above. The preferred substrate is a ceramic that is a ceramic substrate which is made of compacted ceramic powder. This ceramic substrate can be "green" or prefired. The preferred metallic substrate is made of compacted metallic powder. When either of these substrates is used and the coating composition is applied to the substrate, a portion of the solvent is drawn into the porous substrate causing the coating to become somewhat compacted on the substrate and to have integrity. This compaction aids in maintaining the coating on the substrate prior to sintering. When the metallic substrate is a solid metallic material, such as platinum wire and not compacted powder, this phenomenon does not occur and in order to obtain adhesion of the coating to the substrate surface, prior to sintering, it is critical that sufficient binder be used and that the composition be relatively viscous.

Normally the coating step takes place at room temperature. All or a portion of the substrate is coated during this step and is done generally by dipping the substrate in the composition.

The coating thickness is dependent on the viscosity of the composition, the time in which the substrate is maintained in the coating slurry, and the porosity of the substrate being coated. The longer the period of time, the thicker the coating will be. If the coating is too thick volatilization and hence pore formation is inhibited. Furthermore, if the coating is too thick, flaking of the coating can occur. Generally, the substrate will be maintained in the coating composition for 1 second to 1 minute, preferably 5 to 10 seconds.

Generally speaking, the coated substrate is almost immediately placed in the environment where at least a portion of the solvent is volatilized. This allows a thin skin to form on the surface of the coating which assists in pore formation by producing some resistance to the removal of the volatilized solvent bubbles. It, however, does not allow enough time for a thick skin to form which will cause disruption of the coating by causing the coating to flake off during volatilization. Generally no more than 2 minutes, normally only a few seconds, should pass between the coating of the substrate and the volatilizing of the solvent but the time period will vary depending on the thickness of the coating, solvent used, composition used, substrate, etc. The above also is true when perforated articles are being prepared from the composition alone or by placing it on a pyrolyzable substrate.

The volatilization of the solvent occurs when the coated substrate or the composition is contacted with an environment comprising conditions either by high temperature or decreased pressure or a combination thereof to cause the rapid volatilization to occur. Generally with the perforated articles the composition is dropped into the environment in a drop by drop fashion to form spherical type perforated articles. The perforated articles can, however, be prepared by coating a piece of filter paper or other pyrolyzable substrate with the composition and then volatilizing the solvent.

The environment into which the coated substrate or composition is placed is generally a hot bath (80° to 180° C.) of fluorochemical, mineral oil, silicone oil, or vegetable oil. Using heated substrates to contact the composition during the coating causing immediate volatilization, and using less heat in combination with a vacuum to cause volatilization of the solvent can also provide the porosity. A hot flame or microwave oven can also be used.

The preferred method of volatilization is to contact the coated substrate or composition droplets with a fluorochemical bath at from about 130° to about 160° C. The fluorochemical bath comprises a stable, inert, nonpolar, oleophobic and hydrophobic, highly fluorinated liquid at the temperature and pressure of use and usually will be a mixture of compounds having such nature. The fluorocarbons can be straight, chained, branched, or cyclic, or a combination thereof, such as alkylcycloaliphatic, and are preferably saturated, i.e., free of ethylenic or aromatic unsaturation. The skeletal chain of the fluorocarbon can include catenary oxygen and/or trivalent nitrogen hetero atoms bonded only to carbon atoms, such hetero atoms providing stable linkages between fluorocarbon groups and not interfering with the inert character of the fluorocarbon. The fluorocarbon has at least about 7 carbon atoms and may contain 200 or more, the maximum number of carbon atoms being dictated by viscosity. Generally, a range of 7 to 100 will be suitable. Generally, the fluorocarbon will have a boiling range at atmosphere pressure between 80° and 180° C. Generally, the fluorocarbon will contain about 60 to 76 weight percent carbon-bonded fluorine. The fluorocarbon can contain some hydrogen or chlorine, i.e., less than about 5 atom percent on the basis of fluorine content, but is preferably substantially completely fluorinated.

Fluorocarbons useful in this invention are known and readily available, usually as mixtures of fluorocarbons. U.S. Pat. Nos. 3,250,807; 3,250,808; and 3,274,239 disclose fluorinated oils, made by polymerization of perfluoropropylene oxide, which can be stabilized, e.g. as disclosed in U.S. Pat. Nos. 3,214,478; 3,242,218; and 3,342,875, to provide fluorocarbons useful in this invention, said stabilization converting functional or active end groups to inert carbon-bonded hydrogen or fluorine by reaction with fluorinating agents, protic bases, or ultraviolet radiation. U.S. Pat. Nos. 2,500,288; 2,519,983; 2,594,272; and 2,616,927 describe the preparation of inert, highly fluorinated compounds, such as hydrocarbons, ethers, and tertiary amines, said preparation involving electrochemical fluorination in anhydrous HF medium. Commercial fluorocarbons useful in this invention include 3M Company's "Fluorinert" liquids, e.g. FC-40, FC-43, and FC-48, described in that company's bulletins Y-ILBG(R)(187-1)RC and Y-IFC-48(60.2)R.

Generally the coated substrate or composition is maintained in the volatilizing environment for only a short period, from 2 seconds to 2 minutes, for volatilization normally occurs immediately. Thus, there is no reason to maintain the coated substrate or composition in the environment for any additional time. Volatilization of the solvent while providing the porosity also causes some compaction of the composition. After volatilization, the composition must have sufficient integrity to be self-supporting.

After volatilization of at least a portion of the solvent, the coated substrate or perforated articles are placed in a kiln where they are sintered. The temperature of the kiln must be at least that of the sintering temperature of the highest sintering material in the coated substrate or perforated article.

Generally, it is preferred to have the sintering temperature of the powder be substantially the same as that of the substrate so that when the coated substrate is fired, the degree of shrinkage in the substrate and the coating is substantially equal so that adhesion of the coating to the substrate is not hampered. If the sintering temperatures of the coating and substrate vary considerably there will be, in fact, a difference in shrinkage between the two components and good adhesiion is not likely. During sintering, the coating particles sinter with the particles of the substrate causing good adhesion, i.e., a strong bond between the coating and the substrate. If a solid metal substrate is used with a composition containing a ceramic powder or metallic powder with a substantially equivalent sintering temperature, such sintering will also occur.

Preferred substrates are those of compacted ceramic powder made from the ceramic powders detailed above, preferably, aluminum oxide. These are preferably coated with compositions containing the same ceramic powder. A composition containing aluminum oxide on an aluminum oxide substrate is preferred. The metallic substrates are preferably made from powdered metals as detaled above and are coated with compositions containing the same metallic powder.

Normally, sintering will occur between 800° and 1800° C. With the preferred aluminum oxide ceramic powder, the sintering step is accomplished following the heating procedure for Cone Number 31 (Lange, *Handbook of Chemistry,* 10th Edition, New York © 1961, Page 894). During the sintering step the binder, if pyrolyzable, and pyrolyzable substrate, if any, pyrolyzes and is thus removed. The remainder of the solvent, if any, is removed. All that remains is the sintered substrate and coating thereon. In the case of the perforated articles, the sintered composition remains, i.e., the sintered ceramic powder or powdered metal and in some cases, binder.

Generally the size of the pores in the coating of the coated substrate will vary from about 4 to about 350 microns, preferably, from 100 to 200 microns. For prosthetic devices, the pore size must be large enough to allow tissue ingrowth (bone or soft tissue) into the coating on the substrate. Generally a minimum pore size of from 4 to 20 microns is required for such soft tissue ingrowth and from about 125 to 150 microns for bone ingrowth. The pores of the coated substrate and of the perforated articles of the present invention have smooth edges and surfaces and generally are interconnected.

Generally the coating on the substrate is from ½ to 1 millimeter in thickness. In order for there to be tissue ingrowth if the coating is thin, larger diameter pores are required. If the coating is thick and pore size is small, interconnection of the pores is required for ingrowth of tissue.

With the perforated articles, the composition is in a drop by drop fashion placed into the volatilizing environment and then sintered. A single pore is often obtained which is from 20 to 350 microns in diameter. These articles are generally 0.25 to 5 millimeters in diameter.

As noted, the coated substrates are particularly useful in prosthetic devices and can be used to prepare a variety of devices to be implanted into the body including blade vents for dental applications, tooth root implants as well as other prosthetic devices such as hip and finger prostheses, spinal fusion devices, self-anchoring plates, cannulae, etc.

Mechanical fastening by means of a nail which is made of a solid cylindrical ceramic or metallic shaft coated with the coatings of the present invention can be used to attach various materials including bone, wood and metal. The material being fastened tends to compress and spring back to form a lock into the porous coating of the nail.

Perforated articles prepared according to the present invention can be used as catalyst supports, filters, wicks, diffusion control means, and fuel cell dividers.

The perforated articles made by dropping the composition into the environment where volatilization takes place can be used as filler for bone. The articles can be used either singly or in combination with a putty such as a polymeric material, e.g. methyl methacrylate. The articles can also be mixed with Teflon ® implant material, i.e., polytetrafluoroethylene or can be bonded together with polyester or polyolefin to obtain a form which could be implanted into the body. The binder is a material which is inert to the body.

Combinations of body implantable silicone rubber can be used with the perforated articles of the present invention to obtain prosthetic devices which would have attachment means included therein by means of the perforated articles.

Percutaneous devices (devices which are implanted but extend beyond the skin) can be prepared according to the present invention. Percutaneous devices with a coating of the present invention which allow for tissue ingrowth are particularly useful because the tissue surrounding the percutaneous device grows into the device rather than attempting to grow around and under the device (normally called epithelial down-turn); thus, in effect, isolating the device outside the skin or at least not allowing for a seal to be formed between the tissue and the device, sealing the device under the skin. Uses for such devices include blood access for renal dialysis, percutaneous lead shields for pacemakers, etc., peritoneal dialysis, ostomy valves, chronic electrode leads, and implantable devices for chronic drug injections.

A percutaneous device of particular interest is one which has a cylindrical upper portion and a porous skirt. This skirt can be fashioned to fit over a vein. FIG. 1 and 1A depict such a device. FIG. 1 is a perspective view of the percutaneous device. FIG. 1A is a section taken along line 1A—1A of the percutaneous device of FIG. 1. The percutaneous device 1 depicted in FIG. 1 contains cylindrical portion 2 containing porous ceramic coating 3 comprising pores 3a and ceramic 3b. The cylindrical portion 2 also contains Teflon ® plug 4. The cylindrical portion 2 has attached thereto porous ceramic skirt 5 containing pores 6 and ceramic 7. The section view depicted in FIG. 1A shows more clearly the Teflon ® plug 4 and the configuration of the cylindrical portion 2 which comprises porous ceramic coating 3 and ceramic cylinder 8. Ceramic cylinder 8 contains a flared lower portion 9 which retains the paper (not shown) which is used to prepare the void 10 in the skirt 5. The porous coating 5 comprises pores 6, ceramic 7 and central void 10. The void 10 was occupied prior to firing by paper or other pyrolyzable substrate which, upon firing, is decomposed. The particular percutaneous device shown is a vein straddle device wherein the vein fits under the cylindrical portion 2 and through the skirt 5. Tissue grows into the porous skirt 5 from both sides and into the porous ceramic coating 3 on the upper cylindrical portion 2. The tissue growth into the porous ceramic causes the device to be sealed within the skin and prevents epithelial down-turn. The Teflon ® plug seals the implant from the environment during the period when the device is not being used as an access point to the body.

The device is prepared by:

(A) attaching porous absorbent sheet material to a ceramic or metallic substrate, said sheet material being pyrolyzable under the conditions of step (D);

(B) contacting said sheet material and substrate with a composition to provide a coating of said composition on said sheet material and said substrate, said composition comprising as above described;

(C) rapidly volatilizing at least a portion of said solvent of said composition on said sheet material and said substrate;

(D) sintering said coated substrate and the composition on said sheet material to remove said sheet material and to form a percutaneous prosthetic device comprising said substrate with a porous coating and a porous portion attached thereto.

The coated substrates of the present invention because of their method of preparation, particularly the combination of a ceramic composition on ceramic substrate, have very good adhesion of the coating on the substrate. Adhesion is difficult to determine in a quantative fashion as contrasted with a qualitative fashion. However, some indication of the extent of adhesion is capable of being assessed by using a compressive test on the coated substrate. Test method ASTM C 528-71 was utilized on some of the coated substrates in the following examples to determine compressive strength.

The following examples are meant to illustrate but not limit the invention. Parts and percentages are by weight unless otherwise specified. As used in the examples, the following trademarks or tradenames are the following materials:

| | |
|---|---|
| Carboset® 514 (B. F. Goodrich Chemical Co., Cleveland, Ohio) | 30 percent by weight acrylic resin in ammonia water; |
| Al Si Mag® 805 alumina rod (Minnesota Mining and Manufacturing Company, St. Paul, Minnesota) | Pressed alumina rod with an $Al_2O_3$ content greater than 99 percent |
| Al Si Mag® 772 alumina rod (Minnesota Mining and Manufacturing Company, St. Paul, Minnesota) | Pressed alumina rod with an $al_2O_3$ content greater than 99 percent |
| Al Si Mag® 614 ceramic powder (Minnesota Mining and Manufacturing Company, St. Paul, Minnesota) | $Al_2O_3$ content greater than 96 percent |
| Fluorinert® FC-43 (Minnesota Mining and Manufacturing Company, St. Paul, Minnesota | Above described. |

EXAMPLE I

A composition was prepared by mixing together at room temperature the following materials:

| | | |
|---|---|---|
| Al Si Mag® 614 ceramic powder | 18 | gm |
| aluminum stearate powder | 0.5 | gm |
| Polycarbodiimide | 1.0 | gm |
| Carboset® 514 | 2 | gm |
| Water | 3 | cc |
| Propylene glycol | 5 | cc |
| Acetone | 6 | cc |

The prepared composition was immediately coated on a partially prefired solid aluminum oxide core having dimensions of 6.35 × 6.35 × 12.70 mm by dipping the core in the composition. The substrate was maintained in the slurry for about 8 seconds. After coating, the coated core was immediately transferred into a Fluorinert® FC-43 fluorocarbon bath at 150° C. and was maintained in the bath for 10 seconds. The coated substrate was then sintered by placing it into a kiln at 1610° C. for 5 hours. The coated substrate has a porous coating which has an average thickness of 0.79 mm with the average pore size being 200 microns. The coated substrate has a compressive strength of 49,800 $lb/in^2$ (3,500 $kgm/cm^2$) and there was no delamination of the coating until break. Adhesion of the coating was good and the pores has smooth edges and surfaces. The coating has about three to four pores per square millimeter and a total porosity of 24 percent of the area of the surface of the coating.

FIG. 2 is a photomicrograph (magnification—28 times) of the surface of the coating of the core showing the ceramic coating 11 containing pores 12.

Figure 3:
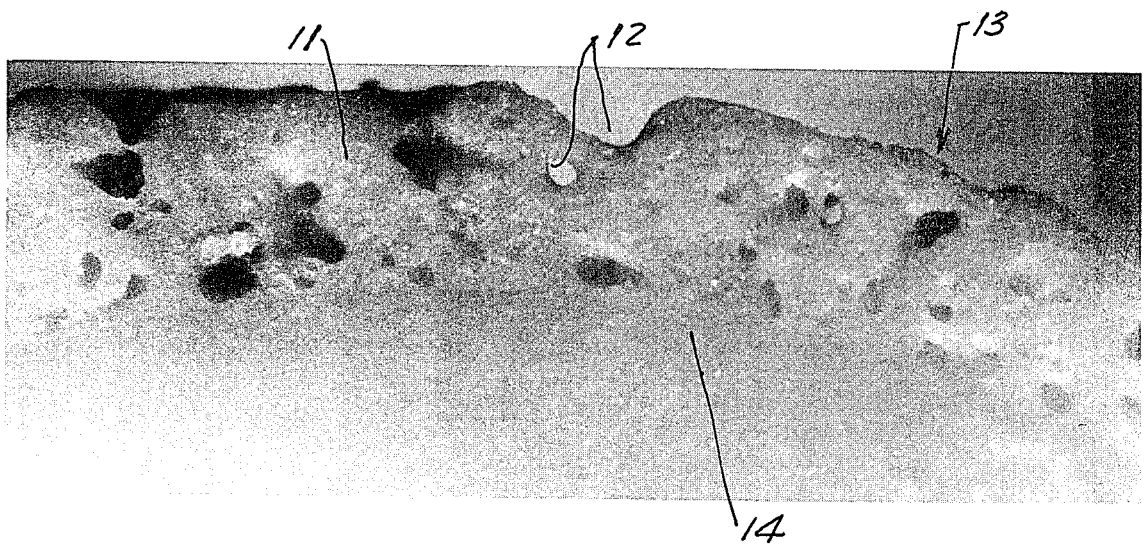

FIG. 3 is a photomicrograph (magnification—60 times) of a section of the coated ceramic core 13 comprising core 14, ceramic coating 11 containing pores 12.

EXAMPLE II

Following the procedure of Example I the following composition was prepared:

| | |
|---|---|
| Al Si Mag® 614 ceramic powder | 18 gm |
| Carboset® 514 | 2 gm |
| Water | 3 cc |

This composition was coated on a solid aluminum oxide partially prefired core of the same size and dimensions as in Example I. The immersion time of the core in the slurry was 60 seconds. The coated core was immediately transferred into a Fluorinert® FC-43 fluorocarbon bath at 150° C. and maintained there for 5 seconds while the water solvent volatilized. The coated core was then sintered at 1610° C. for 5 hours in a kiln. The average pore size in the coating was 200 microns. Adhesion of the coating to the substrate was good. The compressive strength of the coated substrate was 26,800 $lb/in^2$ (1,884 $kgm/cm^2$) and there was no delamination of the coating until break.

EXAMPLE III

A composition was prepared by mixing the following components at room temperature:

| | | |
|---|---|---|
| Al Si Mag® 614 ceramic powder | 9 | gm |
| Aluminum stearate powder | 0.25 | gm |
| Carboset® 514 | 1.0 | gm |
| polycarbodiimide | 0.5 | gm |
| N,N dimethyl formamide | 3.0 | gm |
| Isopropyl alcohol | 2 | cc |

A solid "green" unfired Al Si Mag ® 805 rod, 1.3 centimeters in diameter and 1.9 centimeters long was dipped into the composition for about 5 seconds. The rod was transferred immediately and suspended into a heated (140° C.) bath of Fluorinert ® FC-43 fluorocarbon bath for 20 seconds until the rapid boiling had subsided. The coated articles were fired in an kiln for 4 hours at 1600° C. The coating had an average pore size of 200 microns and the pores had smooth edges and surfaces.

EXAMPLE IV

A composition was prepared with the same components and in the same amounts as in Example III. The composition was dropped in a drop by drop fashion using a dropping funnel into the fluorochemical bath of Example III at 140° C. Perforated articles were obtained. The articles were taken from the fluorochemical bath after approximately b 1 hour. These were immediately fired at 1610° C. for 3 hours to obtain porous ceramic beads. The articles had the following size distribution:

| Percentage retained on screen | Mesh | Size (mm) |
| --- | --- | --- |
| 3.7 | # 10 | 2.00 |
| 44.5 | # 16 | 1.18 |
| 24.1 | # 20 | 0.85 |
| 19.4 | # 40 | 0.41 |
| 4.6 | # 60 | 0.23 |
| 3.6 | less than # 60 | 0.23 |

Figure 4:
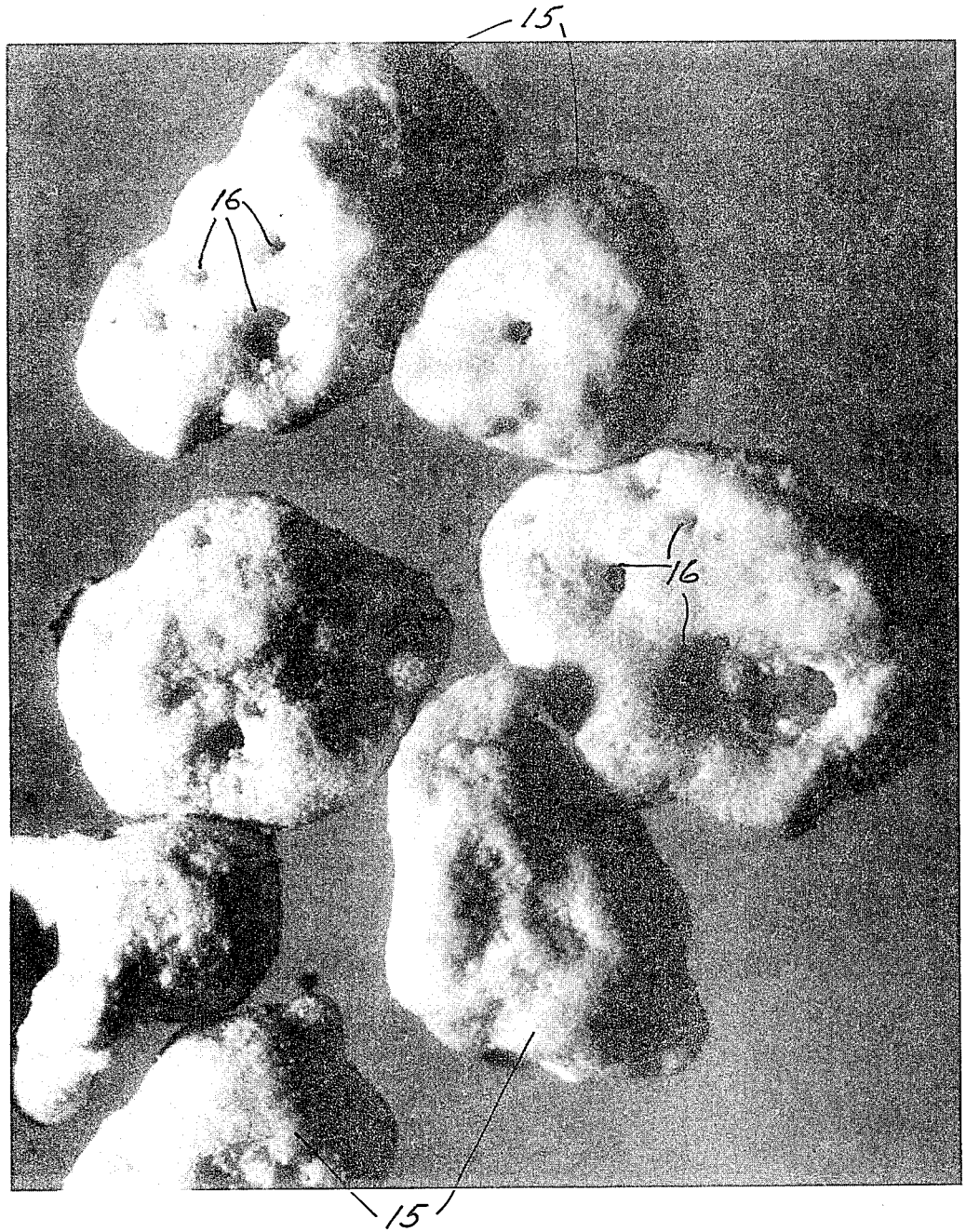

The pores in the articles had an average size of 100 microns. A photomicrograph (magnification—44 times) is shown in FIG. 4 which shows some of the #20 mesh ceramic articles 15 prior to firing containing pores 16.

EXAMPLE V

A composition was made by mixing the following components at room temperature:

| | | |
| --- | --- | --- |
| Al Si Mag® 614 ceramic powder | 9 | gm |
| Styrene-butadiene copolymer latex (30 percent solids) | 1 | gm |
| polycarbodiimide | 0.5 | gm |
| aluminum stearate | 0.25 | gm |
| water | 1 | cc |
| propylene glycol | 1 | cc |
| acetone | 3.5 | cc |

Solid extruded rods of the same type and size as those in Example III were coated with the composition by dipping these rods in the slurry for about 5 seconds. The coated rods were immersed into a hot bath of Fluorinert ® FC-43 fluorocarbon oil at 140° C. for about 20 seconds until boiling subsided. The coated rods were then sintered by placing them into a kiln at 1600° C. for 4 hours. The porous coating had an average depth of ½ to 1 millimeter and an average pore size of 200 microns. The coating had approximately the same pore density as that of Example I.

EXAMPLE VI

Compositions were prepared at room temperature having the following components:

| | Barium Titanate | Corderite | ZrO$_2$ | Spodumene | Electrical Porcelain | Steatite | Ferrites | Alumina |
| --- | --- | --- | --- | --- | --- | --- | --- | --- |
| Ceramic | 9 gms | 9 gms | 9 gms | 9 gms | 9 gms | 9 gms | 9 gms | 9 gms |
| Polycarbodiimide | 0.5 gms | 0.5 gms | 0.5 gms | 0.5 gms | 0.5 gms | 0.5 gms | 0.5 gms | 0.5 gms |
| Carboset® 514 | 1 gm | 1 gm | 1 gm | 1 gm | 1 gm | 1 gm | 1 gm | 1 gm |
| Aluminum Stearate | 0.25 gm | 0.25 gm | 0.25 gm | 0.25 gm | 0.25 gm | 0.25 gm | 0.25 gm | 0.25 gm |
| Water | 1 cc | 5 cc | 1 cc | 1 cc | 2 cc | 2 cc | 1 cc | 1 cc |
| Propylene Glycol | 1 cc | 2 cc | — | 1 cc | 1 cc | 1 cc | 1 cc | 1 cc |
| Acetone | 5.5 cc | 4.5 cc | 4.5 cc | 3.5 cc | 3.5 cc | 5.5 cc | 3.5 cc | 3.5 cc |

The procedure of Example V was followed except that an Al Si Mag ® 772 rod was used and the coated rod was not fired. Porosity in the coating on the rod in each case was substantially that which was obtained in Example V.

EXAMPLE VII

A composition was prepared by mixing the following components at room temperature:

| | | |
| --- | --- | --- |
| Stainless steel powder - 316 L - minus 325 mesh | 9 | gm |
| Aluminum stearate | 0.25 | gm |
| Polycarbodiimide | 0.5 | gm |
| Carboset® 514 | 1 | gm |
| Deionized water | 1 | gm |
| Propylene gycol | 1 | gm |
| Acetone | 1.5 | gm |

Stainless steel substrates (dental blade vents) were injection molded at 70,000 lb./in.$^2$ (4,921 kgm/cm$^2$) from the same type stainless steel powder containing aluminum stearate. The stainless substrates were coated with the afore-mentioned slurry by immersing the substrates into the slurry for about 5 seconds. The coated substrates were then immersed for about 30 seconds in a Fluorinert ® FC-43 fluorocarbon bath at 130° C. The coated substrates were not fired. The coating was porous, about 1 millimeter in thickness and adhered to the substrate.

EXAMPLE VIII

A composition was prepared by mixing the following components at room temperature:

| | | |
| --- | --- | --- |
| Al Si Mag® 614 | 27 | gm |
| Polycarbodiimide | 0.5 | gm |
| Carboset® 514 | 3 | gm |
| Water | 3 | cc |
| Propylene glycol | 3 | cc |
| Acetone | 10.5 | cc |

One additional cc of water was then added. A small (about 8 millimeters in diameter) circle of 3 millimeter thick Soxlett ® pure cellulose filter paper was dipped into the composition for about 5 seconds and them immerged in a 145° C. Fluorinert ® FC-43 fluorocarbon bath. The coated filter paper was fired at 1600° C for 4 hours. The filter paper pyrolyzed during firing. A reasonably strong, porous lattice was obtained which was approximately 2 ½ millimeters thick and about 6 millimeters in diameter. The average weight of the lattice was 70 to 80 milligrams. It had a porous surface and a void center portion where the filter paper had been. The lattice was implanted in the thigh of a rat. Tissue ingrowth was found in the pores and after three months there was no degradation of the lattice while in the rat.

EXAMPLE IX

A composition was prepared by mixing the following components at room temperature:

| | | |
| --- | --- | --- |
| AlPO$_4$ powder (particle size 300 microns or less) | 9 | gms |
| Carboset® 514 | 1 | gm |

-continued

| Polycarbodiimide | 1 gm |
| Water | approx. 2 gms |

A core of the same type and dimensions as Example III was dipped into the composition for approximately 5 seconds. It was then placed in a Fluorinert ® FC-43 fluorochemical bath at 145° C. for approximately 20 seconds. A porous coating on the rod was obtained. The coated rod was then fired at 1600° C. for 4 hours. The porous coating was about 0.7 millimeters thick and had an average pore size of about 300 microns. The pores of the coating had sharper edges and surface than those of Example I.

EXAMPLE X

A composition was prepared by mixing the following components at room temperature:

| Al Si Mag ® 614 ceramic powder | 18 | gm |
| Aluminum Stearate | 0.5 | gm |
| Polycarbodiimide | 1 | gm |
| Carboset ® 514 | 2 | gm |
| Propylene glycol | 2 | gm |
| Water | 3 | cc |
| Acetone | 6 | cc |

A platinum wire of 1 millimeter in thickness was dipped into the composition for 6 seconds and immediately dropped into a hot bath of Fluorinert ® FC-43 fluorocarbon at 150° C. A porous coating of the composition was obtained on the wire. It adhered fairly well to the wire but could be scraped off with a hard instrument. After firing at 1600° C. for 1 hour the platinum fused with the coating at their interface. A porous ceramic on the platinum wire was obtained.

EXAMPLE XI

A percutaneous device for implantation was prepared by machining a solid core of prefired Ai Si Mag ® 772 aluminum oxide into a flared cylindrical shape which is 5/16 inch (8 millimeters) long and 5/32 inch (4 millimeters) in diameter with a 1/16 inch (1.6 millimeter) flare which had a 15/64 inch (6 millimeter) diameter. A piece of Soxlett ® paper 5/8 inch (16 millimeter) by ½ inch (13 millimeter) with a 5/32 inch (4 millimeter) diameter hole in the center was fashioned into a tube with an open slit running the length thereof. The solid core was then inserted into the hole in the paper and the entire composite was dipped for about 3 seconds into a composition which was prepared by mixing the following components at room temperature:

| AlSiMag ® 614 ceramic powder | 9 | gm |
| Polycarbodiimide | 0.5 | gm |
| Aluminum stearate | 0.25 | gm |
| Carboset ® 514 | 1 | gm |
| Water | 1 | cc |
| Propylene glycol | 2 | cc |
| Acetone | 3.5 | cc |

After dipping the coated composite was transferred to a Fluorinert ® FC-43 fluorocarbon bath at 155° C. After the boiling has subsided the coated substrate was removed and dried overnight in a 60° C. oven. Suture holes were formed in the stem of the coated composite and it was fired at 1600° C. for 4 hours. After firing the coated composite was prepared for implanting by pyrolyzing for 3 hours at 600° C. in air to remove organics, by placing it for 3 hours in 50 percent hydrochloric acid solution to remove metal salts and by water washing it for 1 hour in deionized water. After sterilization, the implant was placed through the neck skin of a dog. The implant remained stable and uninfected for the 3 month term of the experiment. Upon removal and microscopic examination, tissue was found to have grown into the porous coating and into and through the cylindrical portion of the skirt thereby anchoring the implant and providing a seal to bacterial invasion (no evidence of epithelial down-turn was noted). The implant had the configuration of the implant shown in FIGS. 1 and 1A except that the ceramic cylinder 8 was solid. Therefore, the Teflon ® plug 4 was not present.

We claim:

1. A method for preparing coated substrates comprising:
    (A) contacting a substrate selected from the class consisting of a ceramic substrate and metallic substrate with a composition to provide a coating of said composition on at least a portion of said substrate, said composition comprising:
        (1) 25 to 80 percent by weight of a material selected from the class consisting of ceramic powder and powdered metal wherein the number average of the longest dimension of the particles of the material is from about 0.1 to about 300 microns;
        (2) 2.0 to 12 percent by weight of a binder capable of adhering said material particles; and
        (3) 18 to 73 percent by weight solvent;
    (B) rapidly volatilizing at least a portion of said solvent of said composition on said substrate to form volatilized solvent bubbles within said composition which escape from said composition and thereby form porosity within said composition and
    (C) sintering said coated substrate to form a coated substrate with a porous coating, said pores of said porous coating being from about 4 to about 350 microns in diameter.

2. The method of claim 1 wherein said material comprises powdered metal selected from the group consisting of stainless steel, titanium, platinum, gold and alloys thereof.

3. A method for preparing ceramic prosthetic device comprising:
    (A) contacting a ceramic substrate with a composition to provide a coating of said composition on at least a portion of said substrate, said composition comprising:
        (1) 25 to 80 percent by weight ceramic powder wherein the number average of the longest dimension of the particles of the ceramic powder is from about 0.1 to about 300 microns;
        (2) 2 to 12 percent by weight of a polymeric binder capable of adhering said ceramic powder particles and pyrolyzable under the conditions of step (C); and
        (3) 18 to 73 percent by weight solvent;
    (B) rapidly volatilizing at least a portion of said solvent of said composition on said substrate to form volatilized solvent bubbles within said composition which escape from said composition and thereby form porosity within said composition; and
    (C) sintering said coated substrate to form a prosthetic device with a porous ceramic coating, said coating being of a sufficient thickness and having pores of a sufficient size to permit tissue ingrowth.

4. The method of claim 3 wherein the ceramic powder is selected from the group consisting of titanate, electrical porcelain, zirconate, cordierate, steatite, ferrite, spodumene, aluminum oxide, aluminum phosphate and calcium phosphates.

5. The method of claim 4 wherein said ceramic powder is aluminum oxide.

6. The method of claim 5 wherein the composition comprises 45 to 65 percent by weight of said ceramic powder, 4 to 8 percent by weight polymeric binder, and 35 to 55 percent by weight solvent.

7. The method of claim 6 wherein step (B) is carried out by placing said coated substrate in an oil bath at from 80° to 180° C.

8. The method of claim 7 wherein the polymeric binder is selected from a group consisting of acrylic polymer, styrene-butadiene copolymer, polyethylene glycol, polycarbodiimide, and polyvinylpyrrolidone.

9. The method of claim 8 wherein step (B) comprises contacting said coated substrate with a bath comprising a member selected from the group consisting of fluorocarbon oil, mineral oil, silicone oil and vegetable oil.

10. The method of claim 9 wherein the composition includes 1 to 4 percent by weight of a salt of a long-chain fatty acid having from 16 to 22 carbon atoms.

11. The method of claim 10 wherein the salt of the long-chain fatty acid is selected from the group consisting of magnesium stearate, calcium stearate, aluminum stearate, magnesium behanate, calcium behanate and aluminum behanate.

12. A prosthetic device comprising a device prepared according to the method of claim 3.

13. The device of claim 12 wherein said device is a percutaneous device and wherein at least a portion of said substrate which is adapted to be placed under the skin is coated with said composition.

14. A method for preparing a perforated article comprising:
(A) preparing a composition comprising:
  (1) 25 to 80 percent by weight of a material selected from the class consisting of ceramic powder and powdered metal wherein the number average of the longest dimension of the particles of said material is from about 0.1 to about 300 microns;
  (2) 2 to 12 percent by weight of a binder capable of adhering said material particles; and
  (3) 18 to 73 percent by weight solvent;
(B) rapidly volatilizing at least a portion of said solvent of said composition to form volatilized solvent bubbles within said composition which escape from said composition and form a porous unfired article, said article containing at least one pore having a diameter from about 20 to about 350 microns in diameter; and
(C) sintering said article.

15. The method of claim 14 which includes the step of separating the composition in droplets prior to step (B).

16. A catalyst support comprising a perforated article prepared according to claim 15.

17. A prosthetic device comprising a perforated article prepared according to claim 15.

18. the prosthetic device of claim 17 which includes the step of coating at least a portion of a substrate which is pyrolyzable under the conditions of step (C) with the composition prior to step (B).

19. A percutaneous device prepared by:
(A) attaching porous absorbent sheet material to a ceramic or metallic substrate, said sheet material being pyrolyzable under the conditions of step (D);
(B) contacting said sheet material and substrate with a composition to provide a coating of a composition on at least a portion of said sheet material and said substrate, said composition comprising;
  (1) 25 to 80 percent by weight of a material selected from the class consisting of ceramic powder and powdered metal wherein the number average of the longest dimension of the particles of the material is from about 0.1 to about 300 microns;
  (2) 2 to 12 percent by weight of a polymeric binder capable of adhering said material particles and pyrolyzable under the conditions of step (D); and
  (3) 18 to 73 percent by weight solvent;
(C) rapidly volatilizing at least a portion of said solvent of said composition on said sheet material and said substrate to form volatilized solvent bubbles within said composition which escape from said composition and thereby form porosity within said composition; and
(D) sintering said coated substrate and the composition on said sheet material to remove said sheet material and to form a percutaneous prosthetic device comprising said substrate with a porous coating and a porous portion attached thereto, said porous coating being of a sufficient thickness and having pores of a sufficient size to permit tissue ingrowth and said porous portion having pores of a sufficient size to permit tissue ingrowth.

20. A prosthetic device comprising a perforated article prepared by:
(A) preparing a composition comprising:
  (1) 25 to 80 percent by weight of a material selected from the class consisting of ceramic powder and powdered metal wherein the number average of the longest dimension of the particles of said material is from about 0.1 to about 300 microns;
  (2) 2 to 12 percent by weight of a binder capable of adhering said material particles; and
  (3) 18 to 73 percent by weight solvent;
(B) rapidly volatilizing at least a portion of said solvent of said composition to form voltalized solvent bubbles within said composition which escape from said composition and form a porous unfired article, said article containing at least one pore being of a sufficient size to permit tissue ingrowth; and
(C) sintering said article.

* * * * *